United States Patent
Bell et al.

(10) Patent No.: US 10,729,553 B2
(45) Date of Patent: Aug. 4, 2020

(54) INTERVERTEBRAL BODY FUSION DEVICE EXPANDED WITH HARDENING MATERIAL

(71) Applicant: Stryker European Operations Holdings LLC, Kalamazoo, MI (US)

(72) Inventors: Christopher P. Bell, New York, NY (US); Agustin Quintana, Montclair, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 16/131,302

(22) Filed: Sep. 14, 2018

(65) Prior Publication Data
US 2019/0083275 A1  Mar. 21, 2019

Related U.S. Application Data

(60) Provisional application No. 62/559,144, filed on Sep. 15, 2017.

(51) Int. Cl.
*A61F 2/44* (2006.01)
*A61B 17/88* (2006.01)
(Continued)

(52) U.S. Cl.
CPC .......... *A61F 2/441* (2013.01); *A61B 17/8847* (2013.01); *A61F 2/442* (2013.01);
(Continued)

(58) Field of Classification Search
CPC ............ A61B 2017/0256; A61B 17/56; A61B 2017/564; A61B 17/8847; A61F 2/44;
(Continued)

(56) References Cited

U.S. PATENT DOCUMENTS 3,875,595 A  4/1975 Froning
4,932,975 A  6/1990 Main et al.
(Continued)

FOREIGN PATENT DOCUMENTS

EP  1442715 A3  11/2004
EP  1415624 B1  5/2006
(Continued)

OTHER PUBLICATIONS

Extended European Search Report for EP18194275.6 dated Feb. 1, 2019.

*Primary Examiner* — Larry E Waggle, Jr.
(74) *Attorney, Agent, or Firm* — Lerner, David, Littenberg, Krumholz & Mentlik, LLP

(57) ABSTRACT

An expandable, intervertebral spacer includes a top component and a base component in engagement with the top component, the base component defining at least one channel for receiving a hardening material, and placement of the hardening material within the channel causes the top component to move between a first position in which the top component is a first distance from the base component and a second position in which the top component is a second distance from the base component, the second distance being greater than the first distance. The hardening material can be removed from the channel by a flexible coring tool, and the top component forced toward the base component to collapse the spacer.

20 Claims, 14 Drawing Sheets

(51) Int. Cl.
*A61F 2/46* (2006.01)
*A61F 2/30* (2006.01)
*A61B 17/70* (2006.01)
*A61B 17/00* (2006.01)
*A61B 17/02* (2006.01)

(52) U.S. Cl.
CPC ............ *A61F 2/447* (2013.01); *A61F 2/4425* (2013.01); *A61F 2/4455* (2013.01); *A61F 2/4465* (2013.01); *A61F 2/4611* (2013.01); *A61B 17/7017* (2013.01); *A61B 2017/00535* (2013.01); *A61B 2017/0256* (2013.01); *A61F 2/4603* (2013.01); *A61F 2002/3055* (2013.01); *A61F 2002/30133* (2013.01); *A61F 2002/30261* (2013.01); *A61F 2002/30405* (2013.01); *A61F 2002/30537* (2013.01); *A61F 2002/30538* (2013.01); *A61F 2002/30548* (2013.01); *A61F 2002/30556* (2013.01); *A61F 2002/30579* (2013.01); *A61F 2002/30581* (2013.01); *A61F 2002/30583* (2013.01); *A61F 2002/30589* (2013.01); *A61F 2002/30593* (2013.01); *A61F 2002/30622* (2013.01); *A61F 2002/30686* (2013.01); *A61F 2002/443* (2013.01); *A61F 2002/4619* (2013.01); *A61F 2002/4631* (2013.01); *A61F 2002/4692* (2013.01); *A61F 2002/4693* (2013.01)

(58) Field of Classification Search
CPC ........ A61F 2/441; A61F 2/442; A61F 2/4425; A61F 2002/443; A61F 2/4455; A61F 2/4465; A61F 2/447; A61F 2002/4475; A61F 2/46; A61F 2/4611; A61F 2/4614; A61F 2002/4631; A61F 2002/4692; A61F 2002/4693
See application file for complete search history.

(56) References Cited

U.S. PATENT DOCUMENTS

| | | | |
|---|---|---|---|
| 4,969,888 A | 11/1990 | Scholten et al. |
| 5,236,460 A | 8/1993 | Barber |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Butterman |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,176,881 B1 | 1/2001 | Schar et al. |
| 6,193,756 B1 | 2/2001 | Studer et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 | 9/2002 | Cohen et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,537,664 B2 | 5/2009 | O'Neill et al. |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 * | 7/2011 | Grotz .................. A61F 2/4465 |
| | | | 623/17.11 |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |
| 8,105,382 B2 | 1/2012 | Olmos et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,353,961 B2 | 1/2013 | McClintock et al. |
| 8,357,104 B2 * | 1/2013 | Moos .................. A61B 10/025 |
| | | | 600/562 |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,632,593 B2 * | 1/2014 | Suh .................... A61F 2/30721 |
| | | | 623/17.12 |
| 8,696,751 B2 | 4/2014 | Ashley et al. |
| 8,932,355 B2 * | 1/2015 | Grotz .................. A61F 2/442 |
| | | | 623/17.16 |

(56) References Cited

U.S. PATENT DOCUMENTS

| | | |
|---|---|---|
| 9,028,550 B2 | 5/2015 | Shulock et al. |
| 9,135,374 B2 | 9/2015 | Jones et al. |
| 9,180,010 B2 | 11/2015 | Dong et al. |
| 9,456,901 B2 | 10/2016 | Jones et al. |
| 2001/0056302 A1 | 12/2001 | Boyer et al. |
| 2002/0128716 A1 | 9/2002 | Cohen et al. |
| 2002/0136146 A1 | 9/2002 | Lee et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2003/0130739 A1 | 7/2003 | Gerbec et al. |
| 2004/0030346 A1 | 2/2004 | Frey et al. |
| 2004/0088054 A1 | 5/2004 | Berry |
| 2004/0097928 A1 | 5/2004 | Zdeblick et al. |
| 2004/0133273 A1 | 7/2004 | Cox |
| 2004/0148028 A1* | 7/2004 | Ferree ................ A61F 2/4425 623/17.11 |
| 2004/0181229 A1 | 9/2004 | Michelson |
| 2004/0186576 A1 | 9/2004 | Biscup et al. |
| 2005/0033437 A1 | 2/2005 | Bao et al. |
| 2005/0043800 A1 | 2/2005 | Paul et al. |
| 2005/0049590 A1 | 3/2005 | Alleyne et al. |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0149377 A1 | 7/2006 | Navarro et al. |
| 2006/0167547 A1 | 7/2006 | Suddaby |
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1 | 10/2007 | Grotz et al. |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0215153 A1 | 9/2008 | Butterman et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2011/0130835 A1 | 6/2011 | Ashley et al. |
| 2011/0270398 A1 | 11/2011 | Grotz et al. |
| 2011/0288646 A1 | 11/2011 | Moskowitz et al. |
| 2012/0116518 A1 | 5/2012 | Grotz et al. |
| 2012/0245695 A1 | 9/2012 | Simpson et al. |
| 2013/0190875 A1 | 7/2013 | Shulock et al. |
| 2014/0081404 A1* | 3/2014 | Jacofsky ................ A61F 2/447 623/17.16 |
| 2015/0112352 A1 | 4/2015 | Krause et al. |

FOREIGN PATENT DOCUMENTS

| | | | |
|---|---|---|---|
| WO | 2003003951 | A1 | 1/2003 |
| WO | 2004016250 | A1 | 2/2004 |
| WO | 2004016205 | A3 | 5/2004 |
| WO | 2006044786 | A3 | 1/2007 |
| WO | 2008011371 | A3 | 3/2008 |
| WO | 2007124078 | A3 | 7/2008 |
| WO | 2008039811 | A3 | 7/2008 |
| WO | 2008103466 | A1 | 8/2008 |
| WO | 2008112607 | A3 | 12/2008 |
| WO | 2008148210 | A1 | 12/2008 |
| WO | 2009033100 | A1 | 3/2009 |
| WO | 2009064787 | A2 | 5/2009 |
| WO | 2008121251 | A3 | 8/2009 |
| WO | 2009105182 | A1 | 8/2009 |
| WO | 2008086276 | A3 | 12/2009 |
| WO | 2010074704 | A1 | 7/2010 |
| WO | 2010068725 | A3 | 10/2010 |
| WO | 2011150077 | A1 | 12/2011 |

\* cited by examiner

INTERVERTEBRAL BODY FUSION DEVICE EXPANDED WITH HARDENING MATERIAL

CROSS-REFERENCE TO RELATED APPLICATIONS

This application claims the benefit of the filing date of U.S. Provisional Patent Application No. 62/559,144 filed Sep. 15, 2017, the disclosure of which is hereby incorporated herein by reference.

BACKGROUND OF THE INVENTION

The present disclosure relates generally to implants, instrumentation, kits and methods for spinal surgery. More particularly, the present disclosure relates to expandable intervertebral body fusion devices for spinal surgery.

Back pain can be caused by several problems affecting the spinal vertebral discs, including, for example, degeneration, bulging, or herniating. The pain is attributable to friction or pressure that occurs when one or both vertebrae adjacent a disc exert uneven pressure on that disc, which can in turn irritate nearby nerve tissue. A typical remedy for a disc problem is to perform a cervical, thoracic or lumbar fusion (all generally referred to as "IF" herein) surgery utilizing an interbody or intervertebral implant. This type of surgery is intended to immobilize and ultimately fuse the two vertebrae on either side of the defective disc to form a single, solid bone mass.

Generally, in existing IF surgery, at least part of the defective disc is removed from the patient, the vertebrae are returned to their normal spacing, and a spinal implant device is inserted into that space to maintain the spacing and provide support to the adjacent vertebrae. The implant may be filled with bone graft material to promote fusion, and in certain instances, the intervertebral space may be provided with additional bone graft material.

Included among different types of intervertebral implants are expandable implants. Such implants often have an initially contracted configuration, such that they have a low profile in the superior-inferior direction, for ease of insertion into the intervertebral space. Such expandable implants can then be expanded in the superior-inferior direction after implantation, so as to securely engage and stabilize the vertebrae on both sides of the intervertebral space. Some such implants include mechanically locking mechanisms to lock the implant in the expanded configuration; however, these implants are difficult to manufacture, assemble, deploy and lock in situ. Moreover, should a surgeon determine the implant has been expanded too much or upon removal of the device in a revision, reduction in the height of such implants can often be difficult. Thus, there is a need for an expandable implant capable of easy in situ expansion and contraction.

BRIEF SUMMARY OF THE INVENTION

A first aspect of the present disclosure is an expandable, intervertebral spacer including a top component, a base component in engagement with the top component, the base component defining at least one channel for receiving a hardening material, with placement of the hardening material within the channel causing the top component to move between a first position in which the top component is a first distance from the base component and a second position in which the top component is a second distance from the base component, the second distance being greater than the first distance.

In other embodiments, the spacer may include an injection port in fluid communication with the at least one channel of the base component. The spacer may include a locking mechanism engageable with the injection port. The locking mechanism may be adapted to seal the hardening material in the spacer. The locking mechanism may be a threaded plug. When the hardening material hardens, the spacer may be rigid. The top component may be moveable with respect to the base component before the hardening material hardens. The top component may be connected to the base component by at least one securing member, the securing members configured to allow the top plate to move in the different directions. The securing member may be a post including a rounded member connected to a first end of a shaft and a flange connected to a second end of the shaft. A diameter of the shaft of the post may be less than a diameter of the flange of the post. The top component may define a first hole for engaging the rounded member of the post and the base component may define a second hole for engaging the flange of the post. The second hole may include a step having a diameter less than the diameter of the flange, such that the step prevents the flange from translating out of the second hole. The at least one channel of the base component may be curved. The base component may include an internal cavity for receiving the top component, the internal cavity in fluid communication with the channel. A diameter of the channel may be greater than a diameter of the internal cavity.

In still other embodiments, any of the expandable spacers may be included in a kit for spinal surgery. The kit may include the spacer and a coring tool adapted to remove the hardening material from the spacer after the hardening material has hardened. The kit may include the hardening material.

A second aspect of the present disclosure is a system for inserting and expanding an intervertebral spacer, the system including a plug engageable with the spacer, a shaft having a first end connected with the plug, a handle connected to a second end of the shaft, and an inserter having a distal end connectable with an aperture of the spacer and defining a channel, the channel in fluid communication with a one-way pressure valve, the operation of the handle causes the shaft to advance through the channel.

In other embodiments, the system may include an expandable intervertebral spacer that is expandable through the introduction of the fluid. The system may include a collection tube for collecting excess fluid, in which fluid that flows into the valve must flow into the collection tube. The collection tube may be detachable and disposable. The distal end of the shaft may be a split tip.

Another aspect of the present disclosure is a method of implanting and expanding an expandable, intervertebral spacer in the intervertebral disc space between two adjacent vertebrae including inserting the spacer at least partially into the intervertebral disc space, and inserting hardening material into a channel of a base component of the spacer, the hardening material causing a top component of the spacer to move a distance from a first position to a second position, the top component being relatively further from the base component in the second position than in the first position.

In other embodiments, the method may include plugging the channel. The top component may include a top plate, and the method may include moving the top plate in a posteranterior direction and/or lateral direction before the hardening material hardens.

Another aspect of the present disclosure is a method of implanting and expanding an expandable, intervertebral spacer in the intervertebral disc space between two adjacent vertebrae including providing an expandable spacer including a top component and a base component in engagement with the top component, the base component defining at least one channel for receiving hardening material, the top component being movable between a first position in which the top component is a first distance from the base component, and a second position in which the top component is a second distance from the base component, the second distance being greater than the first, and with the hardening material in the at least one channel, the top component is in the second position, inserting the spacer at least partially into the intervertebral disc space, and inserting the hardening material into the channel causing the top component to move to the second position.

Another aspect of the present disclosure is a method for collapsing an expanded spacer inserted within intervertebral disc space including removing a plug from the spacer, coring out hardened material positioned within a channel of a base component of the spacer and collapsing a top component in a direction toward a base component of the spacer to reduce the height of the spacer.

In other embodiments, the channel may be curved. The coring step may be performed using a coring tool having a flexible portion adapted to fit in the curved channel. Removing the plug may include rotating the plug approximately 90 degrees in a counter-clockwise or clock-wise direction.

DETAILED DESCRIPTION

As used herein unless stated otherwise, the term "anterior" means toward the front part of the body and, the term "posterior" means toward the back part of the body. When referring to specific directions in the following discussion of a certain device, the terms "proximal" and "distal" are to be understood in regard to the device's orientation and position during exemplary application to human body. Thus, the term "proximal" means closer to the operator or in a direction toward the operator, and the term "distal" means more distant from the operator or in a direction away from the operator. In addition, the terms "about," "generally" and "substantially" are intended to mean that slight deviations from absolute are included within the scope of the term so modified.

Different interbody fusion procedures can be distinguished based on the location along the spine (e.g., in the cervical, thoracic, or lumbar regions), the type of implant used, and the surgical approach to the intervertebral space. Different surgical approaches to the spine include anterior, posterior, and lateral. Examples of interbody fusion techniques performed along a posterior approach include transforaminal lumbar interbody fusion (TLIF) and posterior lumbar interbody fusion (PLIF).

Generally, in TLIF, one intervertebral implant is positioned into the intervertebral space from the posterior of the patient, but the spine is approached from a more posterior-lateral position of the body. Typically, implants used in these TLIF techniques are often curved and may have a kidney bean shape.

Generally, in PLIF, two intervertebral implants are positioned within the intervertebral space along a posterior-anterior direction, with one implant positioned toward the left side of the spine and one implant positioned toward the right side of the spine. Typically, the implants used in these PLIF techniques have a straight shape and extend along a central axis.

Lateral approach interbody fusion surgeries generally utilize implants that are generally symmetric along their longitudinal axis and may have a rectangular or oval shape. These implants cover a substantial portion of intervertebral space and are commonly larger than those used in TLIF or PLIF surgeries.

Figure 1:
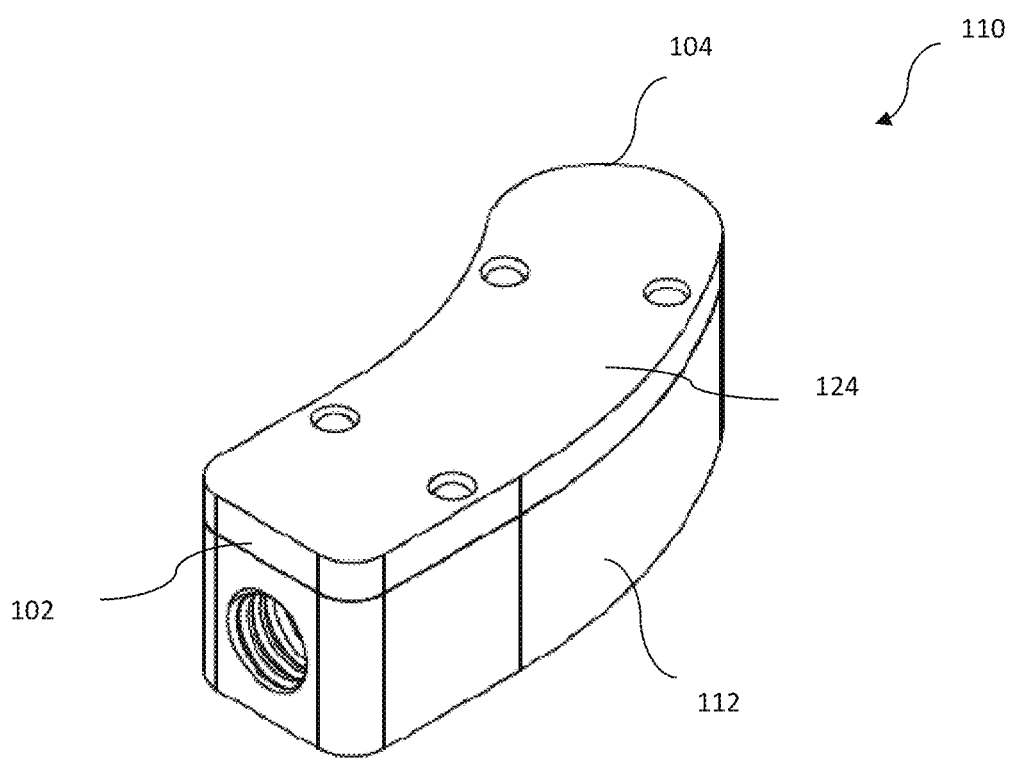
FIG. 1 is a perspective front view of an expandable intervertebral spacer, in a collapsed condition, according to an embodiment of the present disclosure.
Figure 2:
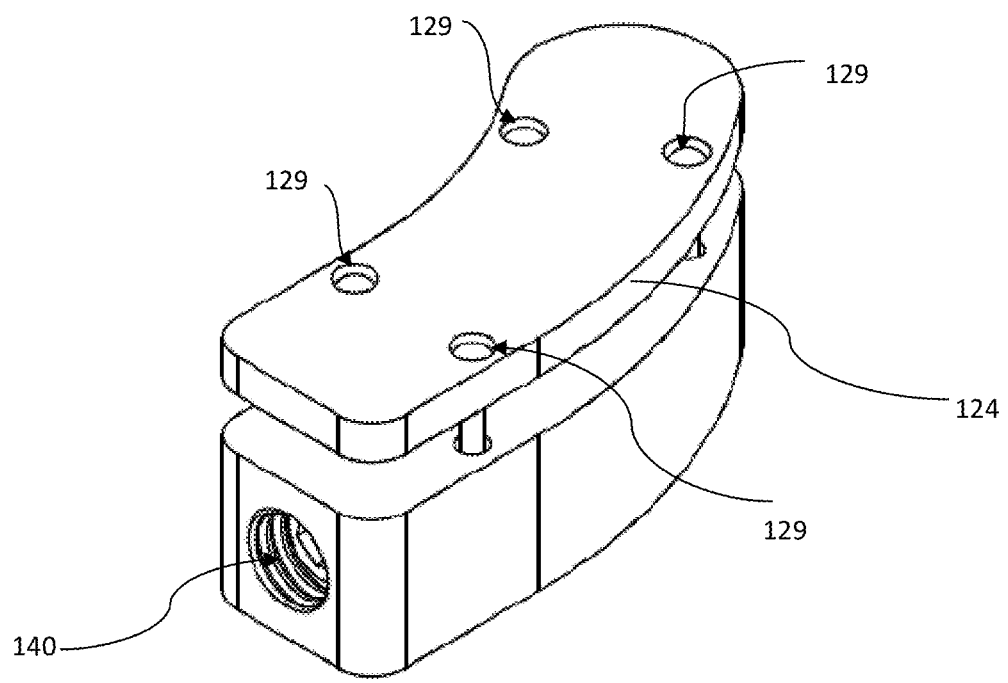
FIG. 2 is a perspective front view of the spacer of FIG. 1, in an expanded condition.

Referring to FIGS. 1-8, an expandable intervertebral implant or spacer 110 according to an embodiment of the present disclosure can be hydraulically expanded from a collapsed condition, in FIG. 1, in which the spacer has a relatively low profile, to an expanded condition, in FIG. 2, in which the spacer has an increased height dimension. The spacer 110 allows for hardening material, such as bone cement, to be introduced after implantation of the spacer into the intervertebral disc space in order to cause the expansion of the device. Due to the hydraulic expansion, spacer 110 can be optimally sized for placement through a small incision and securement and engagement with the adjacent vertebrae after expansion. Additionally, the use of hardening material allows the implant to lock at a variety of heights and angles within the intervertebral space to fit the needs of the patient's anatomy. After injecting the implant with the hardening material, the material hardens and sets, such that the implant becomes a rigid expanded spacer. As will be described in greater detail below, a coring tool can be used during a revision surgery to core and remove the hardening material from the spacer to reduce the height dimension or positioning of the spacer based on the patient's needs.

Spacer 110 is specifically designed to be used in TLIF techniques, as it has a generally kidney bean shape extending between a posterior end 102 and an anterior end 104. Spacer 110 includes base component 112 in engagement with top component 124, and locking mechanism or plug 140 (see FIG. 9). In alternative embodiments, in a side view, top and base components 124, 112 may be curved or angled to allow spacer 110 to restore the natural lordotic angle between adjacent vertebral bodies.

Figure 3:
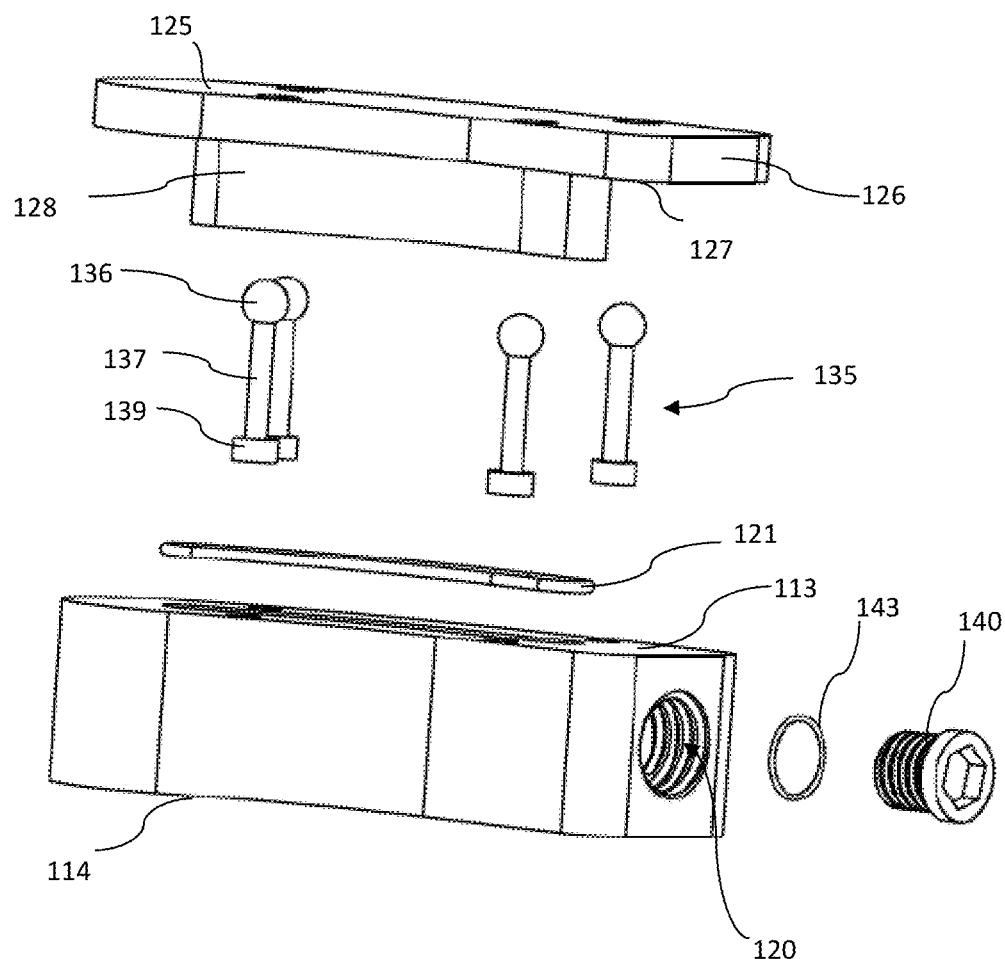
FIG. 3 is an exploded view of the spacer of FIG. 1.
Figure 4:
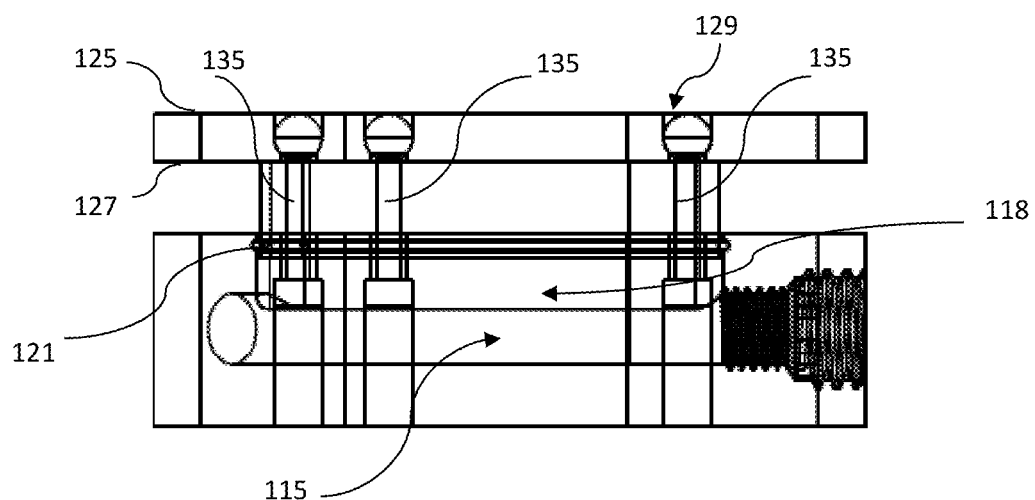
FIGS. 4-5 are wireframe and cross-sectional side views, respectively, of the spacer of FIG. 1.

With reference to FIGS. 2-3, top component 124 includes plate 126 and leg 128 extending inferiorly from lower surface 127 of the plate 126. In the illustrated embodiment, leg 128 has a generally curved shaped in the same form as are the lateral sides of top plate 126. Top plate 126 includes holes 129 extending through the plate from upper surface 125 to lower surface 127. As shown in FIG. 4, a diameter of a hole 129 at upper surface 125 is greater than a diameter of the hole at lower surface 127. In this manner, each hole 129 tapers slightly inwardly from upper surface 125 to the lower surface of the plate 126. Alternatively, hole 129 can exhibit a constant larger diameter at upper surface 125 to form a countersink of sorts.

Holes 129 are sized and configured to receive securing members or posts 135. Posts 135 include rounded or spherical portion 136, shaft 137 and flange or end portion 139. End portion 139 has a diameter greater than the diameter of at least shaft 137 and may be generally shaped as a rectangle, oval, circle or triangle. Each spherical portion 136 of a post 135 is received within a hole 129, and due to the slight taper of the holes, the spherical portion 136 is maintained within plate 126. However, because of the spherical configuration of portion 136, plate 126 can move slightly relative to the post 135, which can allow for some movement of plate 126 with respect to base component 112. This slight movement may enable spacer 110 to optimize its fit and securement between the top plate and the end plate of the adjacent vertebrae. The movement can occur about the horizontal and/or longitudinal axes of the spacer 110, such as, for example, in the posterior-anterior and/or lateral directions. In this manner, the top component may be moved such that the top component is not parallel with the base component.

In an alternative embodiment, holes 129 may extend into the plate 126 from lower surface 127 but not extend through upper surface 125. Spherical portion 136 can fit within the hole and allows for movement in the same manner as described above.

Base component 112 includes upper and lower surfaces 113, 114, respectively and slots or internal cavities 118 extending through a portion of upper surface 113 and into the base component. Internal cavity 118 is sized and shaped to receive and removably retain leg 128 of the top component 124 within the internal cavity. Therefore, at least a portion of the external dimensions of leg 128 are less than the internal dimensions of the internal cavity 118 of the base component. For instance, clearance exists between leg 128 and the side walls 117 (see FIG. 7) surrounding internal cavity 118, which enables leg 128 of top component 124 to smoothly translate in the superior-inferior direction and the top component to have some relative movement relative to the base component 112. In one embodiment, internal cavity 118 includes a circumferential recess for accommodating a seal 121 (e.g. an O-ring) to retain the internal pressure of the system during expansion of the spacer.

Additionally, base component 112 includes holes 119 extending inferiorly from upper surface 113 into the base component along a longitudinal axis. Each hole 119 is sized and configured to receive a corresponding post 135, and each hole 119 substantially aligns with a hole 129 of the top component 124. When positioned in a hole 119, posts 135 can move in the superior-inferior direction during expansion/contraction. The movement of a post 135 within a hole 119 may be limited by a step formed in the hole, such that the diameter of the step is smaller than the diameter of end portion 139 of post 135. In this manner, end portion 139 of post 135 can contact the step and prevent movement of the post past the step. This prevents separation of top component 124 from base component 112 during expansion, as well as limits the overall expansion capability of the device. In the illustrated embodiment, spacer 110 includes four holes 119 of base component 112, four holes 129 of top component 124, and four corresponding posts 135, although, any number of holes and posts can be included and preferably three or more of each are included in the spacer.

Figure 5:
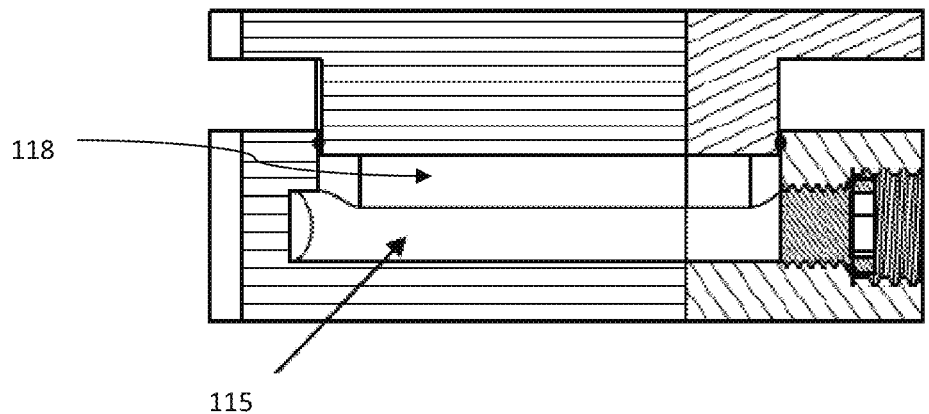
Figure 6:
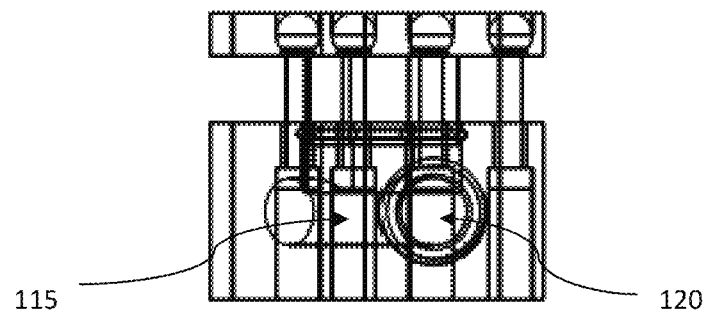
FIGS. 6-7 are wireframe and cross-sectional front views, respectively, of the spacer of FIG. 1.
Figure 7:
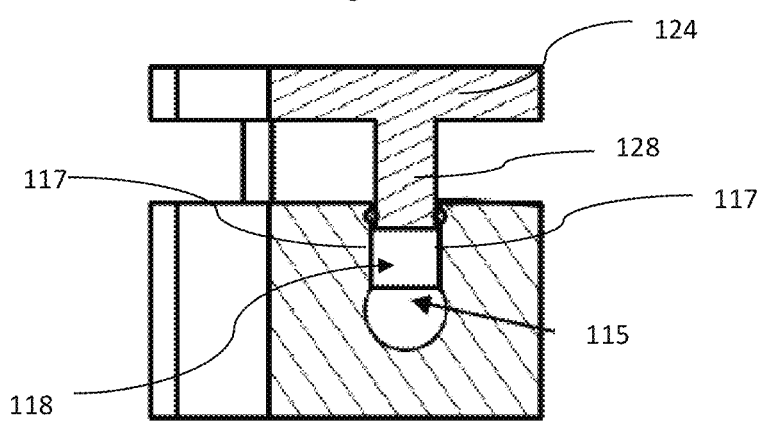
Figure 8:
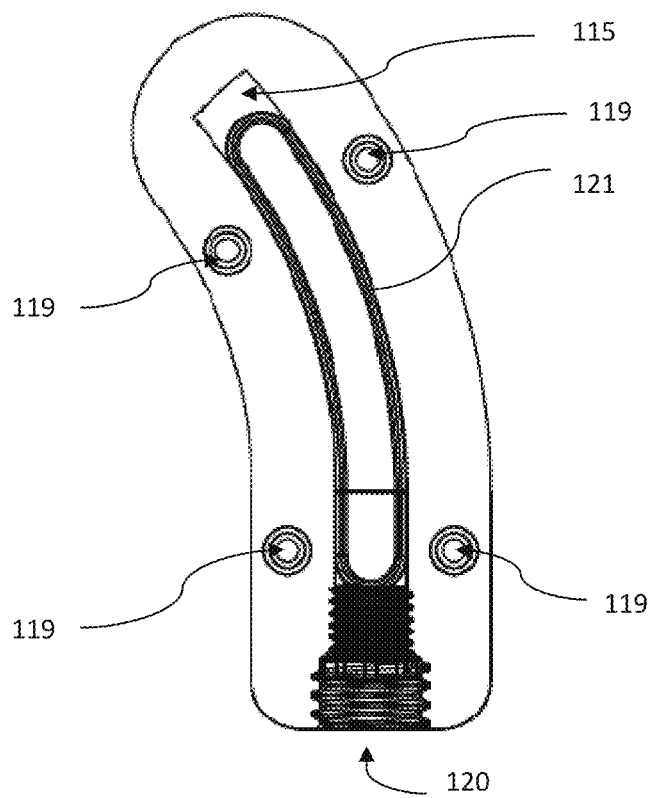
FIG. 8 is a wire frame top view of the spacer of FIG. 1.

Base component 112 also includes hydraulic pressure chamber or channel 115 in fluid communication with internal cavity 118. The diameter of channel 115 is equal to or greater than the diameter of the internal cavity 118 as in FIG. 7, so that enough hardening material is removed to allow for collapsing of the spacer 110, as is discussed below. In the illustrated embodiment, internal cavity 118 and channel 115 are curved, however, in other examples, they can be straight. As shown in FIGS. 4-5, channel 115 extends further anteriorly than internal cavity 118. Base component 112 also includes injection port or opening 120 for injection of hardening material and for receiving plug 140. Injection port 120 is positioned on posterior end 102, such that it can be accessed from a posterior approach during surgery. Injection port 120 has a perimeter at a location about a central axis of the port that is fully enclosed within the base component. In the illustrated embodiment, port 120 is annular, and may be circular. Although, in other examples, the port can be any shape and size suitable to receive a plug 140. In one embodiment, injection port 120 may be threaded for threaded engagement with plug 140. Injection port 120 leads into channel 115 such that material injected into the base component at the injection port 120 flows into channel 115 and internal cavity 118. Plug 140 is adapted to be received within injection port 120 after spacer 110 has been expanded to maintain the internal pressure within the expanded spacer and to prevent the hardening material from leaking out of the spacer. At least one seal 143 (e.g. an O-ring) is positioned around the circumference of the plug to retain the internal pressure of the system and the hardening material within the spacer 110 when securing the plug 140 to the injection port. Additionally, plug 140 is made from a material that does not adhere to the bone cement, such that the plug can be removed, such as, for example, during a revision surgery.

Figure 9:
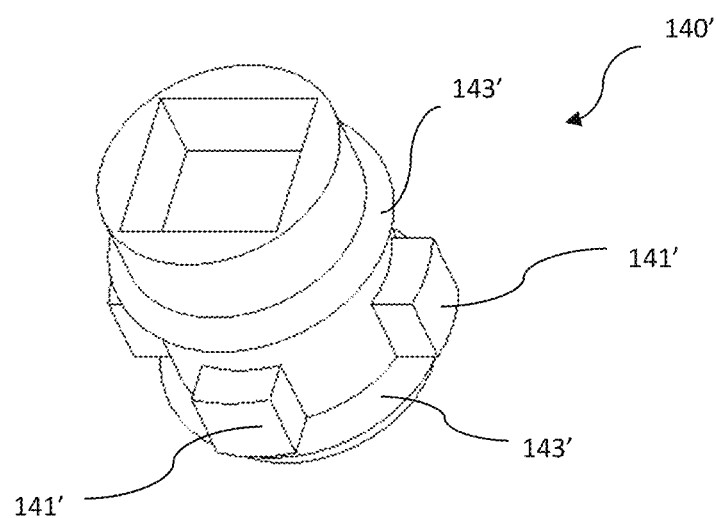
FIG. 9 is a perspective top view of an alternate embodiment of a locking mechanism to be used in conjunction with the spacer of FIG. 1 according to another embodiment of the present disclosure.

FIG. 9 shows an alternate embodiment of a plug 140'. Plug 140' includes projections 141' spaced apart on the circumference of the plug. In the illustrated embodiment, there are four projections spaced substantially equally apart on the circumference. Further plug 140' includes more than one, and preferably three seals or O-rings 143'.

The spacer 110 can be comprised of a porous metal such as the porous titanium alloy provided by Howmedica Osteonics Corporation under the tradename Tritanium®. The porous metal can be included on any surface of the spacer 110. The implant systems may be comprised of metal, such as titanium, ceramic, glass, polymer, or any other material known for use in the human body and capable of utilization in a 3D printing technique. The implant systems may also comprise one or more surface treatments to encourage bony attachment, such as porous coating, plasma spray coating, hydroxyapatite, or tricalcium phosphate. Of course, any of the spacers according to the present invention may also be fabricated from more traditional manufacturing processes like molding and machining.

An alternate embodiment of a spacer 210 is shown in FIGS. 10-13. Like numerals refer to like elements in this embodiment, but with numbers in the 200-series. Because of the similarities, only the differences between spacers 110, 210 will be discussed below.

Figure 12:
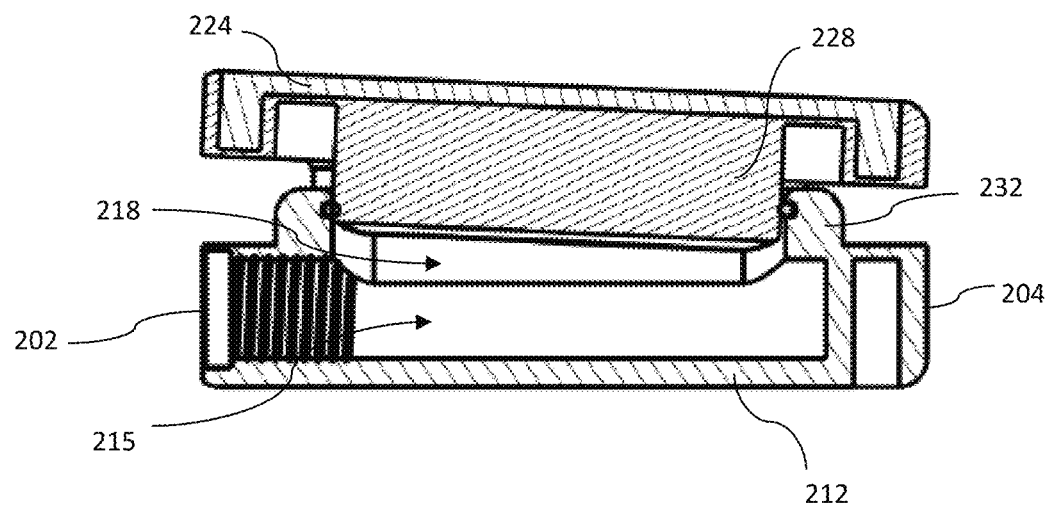
FIGS. 12-13 are side and front cross section views, respectively, of the spacer of FIG. 11.

Spacer 210 can be used in PLIF techniques, as it has a generally rounded oval shape. In other embodiments, the spacer can be in the shape of a rectangle. As shown in FIG. 12, base component 212 of the spacer 210 includes raised portion 232 in which internal cavity 218 is disposed. Leg 228 of top component 224 is positioned and can translate within internal cavity 218. The distance or length channel 215 extends into base component 212 from posterior end 202 toward anterior end 204 is greater than the distance or depth that internal cavity 218 extends into the base component, measured along the same direction. Further, the diameter of channel 215 along its length is equal to or greater than the diameter of the internal cavity along the length of the internal cavity. In the embodiment, the channel 215, internal cavity 218, and leg 228 may be straight or curved.

Figure 10:
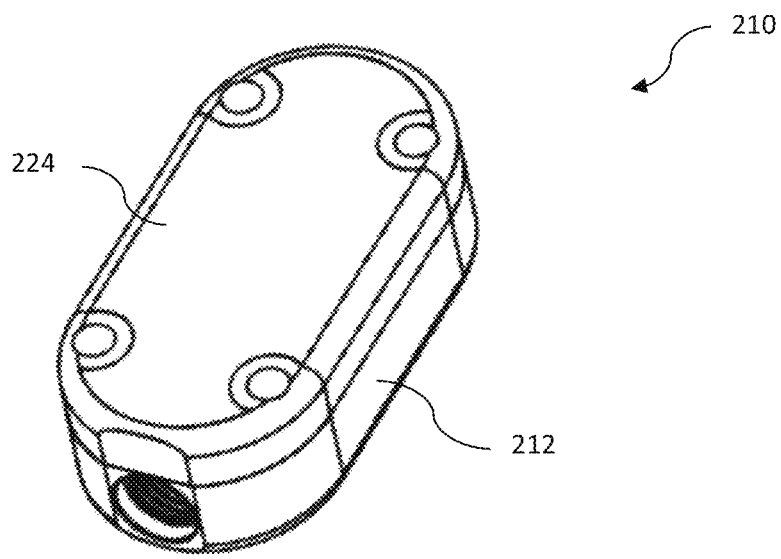
FIGS. 10-11 are front perspective views of an expandable spacer, in a collapsed condition and an expanded condition, respectively, according to another embodiment of the present disclosure.
Figure 11:
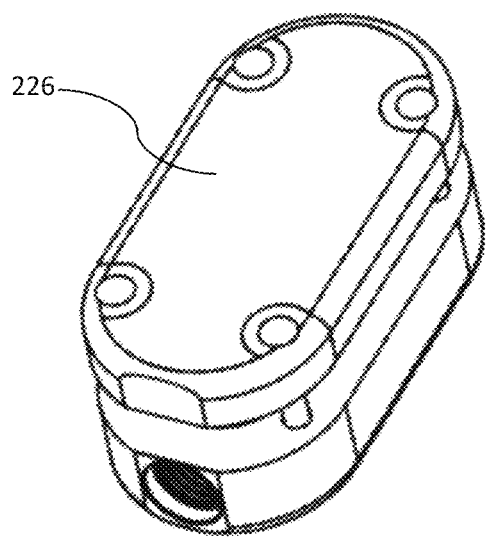
Figure 13:
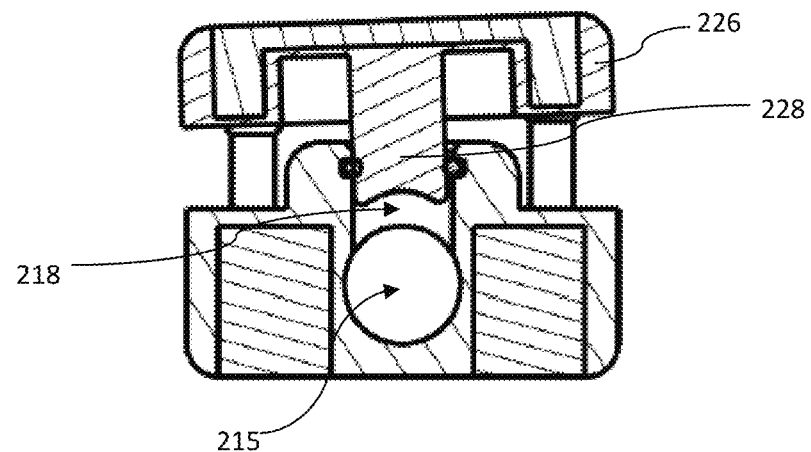

FIG. 10 shows spacer 210 in the collapsed condition and FIG. 11 shows the spacer in the expanded condition. In one embodiment, as shown in FIG. 12, spacer 210 is in the expanded condition with hardening material in channel 215 and internal cavity 218. In this embodiment, top component 224 (e.g. top plate 226 and leg 228) is angled in the posterior-anterior direction, and FIG. 13 shows the top plate angled in the lateral direction. With the material hardened, spacer 210 is set in these positions, with the top component maintaining the angle shown. In this manner, the top plate can be adjusted and angled in situ to better engage with the adjacent vertebrae.

Figure 14:
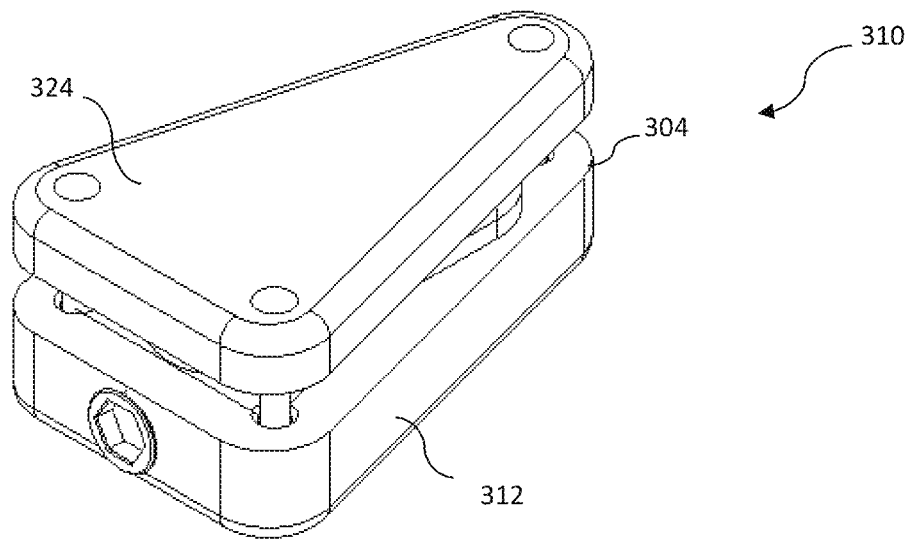
FIGS. 14-15 show a front perspective view and an exploded view, respectively, of an expandable spacer according to another embodiment of the present disclosure.
Figure 15:
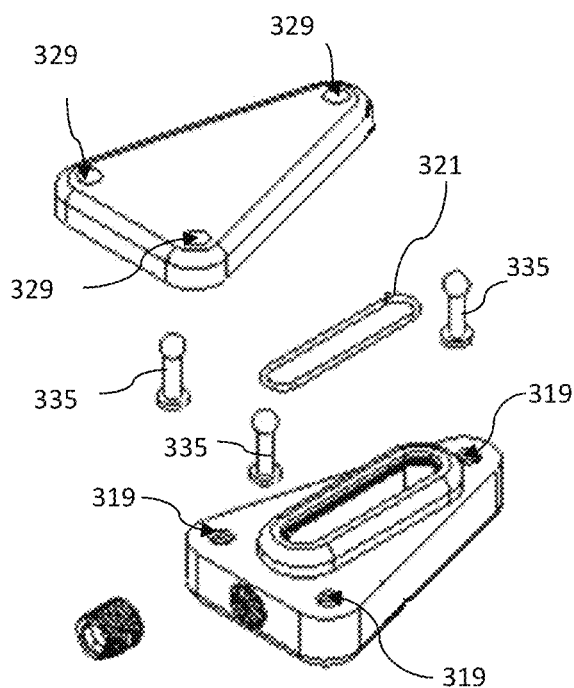

An alternate embodiment of a spacer 310 is shown in FIGS. 14-15. Like numerals refer to like elements in this embodiment, but with numbers in the 300-series. Again, only the differences between spacers 210, 310 will be discussed.

Spacer 310 has a generally triangular shape with the spacer tapering toward anterior end 304. Spacer 310 includes three spaced apart holes 319 of base component 312, holes 329 of top component 324, and posts 335.

Figure 16:
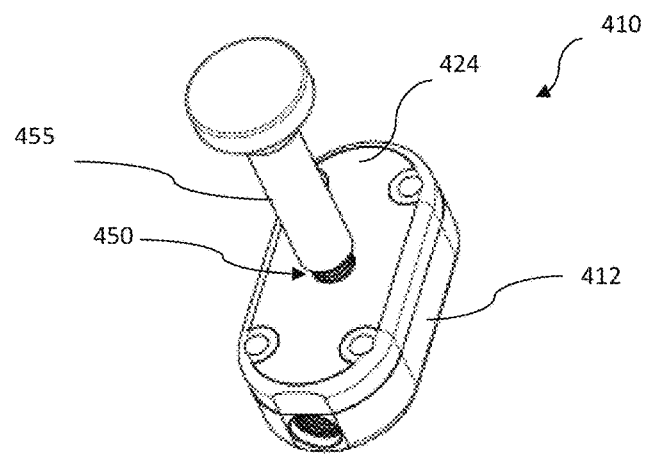
FIG. 16 shows a side perspective view of an expandable spacer according to yet another embodiment of the present disclosure.

A further alternate embodiment spacer 410 is shown in FIG. 16. Spacer 410 includes opening 450 for receiving syringe 455. Syringe 455 can inject biologics, such as, for example BMA, allograft, autograft, synthetics or the like. The biologics can be injected between top component 424 and base component 412 and packed around the spacer for better bone ingrowth.

In other embodiments, each of the above-described spacers may include openings or windows on the top and/or base components for receiving bone in-growth material.

In preferred arrangements, any of the present implants can be formed, at least in part, in a layer-by layer fashion using an additive layer manufacturing (ALM), i.e. three-dimensional (3D) printing, process using a high energy beam, such as a laser beam or an electron beam. Such ALM processes may be but are not limited to being powder-bed based processes including but not limited to selective laser sintering (SLS), selective laser melting (SLM), and electron beam melting (EBM), as disclosed in U.S. Pat. Nos. 7,537,664 and 9,456,901, the disclosures of each of which are hereby incorporated by reference herein, or other ALM processes such as but not limited to powder-fed based processes including but not limited to fused filament fabrication (FFF), e.g., fused deposition modeling (FDM).

The implants may be constructed of porous geometries which have been digitally modeled using unit cells, as further described in U.S. Pat. Nos. 9,180,010 and 9,135,374, the disclosures of each of which are hereby incorporated by reference herein. A first layer or portion of a layer of powder is deposited and then scanned with a high energy beam to create a portion of a plurality of predetermined unit cells. Successive layers of powder are then deposited onto previous layers of the powder and also may be individually scanned. The scanning and depositing of successive layers of the powder continues the building process of the predetermined porous geometries. As disclosed herein, by continuing the building process refers not only to a continuation of a porous geometry from a previous layer, but also a beginning of a new porous geometry as well as the completion of a porous geometry. The porous geometries of the formed porous layers may define pores that may be interconnecting to provide an interconnected porosity. Of course, implants can also be made to be solid with or without porous portions.

Figure 17:
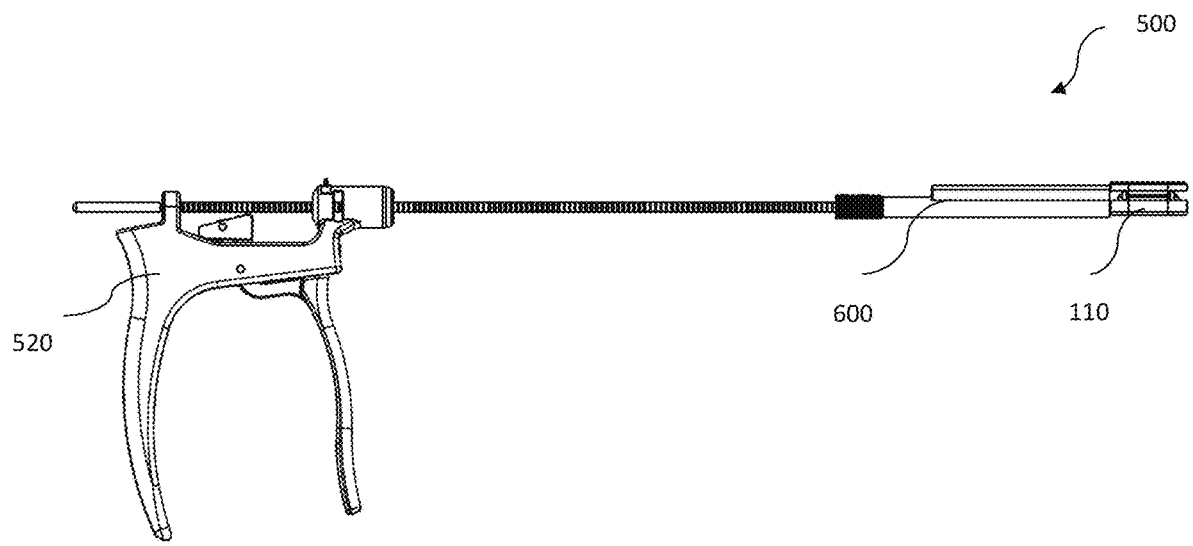
FIGS. 17-19 are perspective and wireframe side views, respectively, of an insertion instrumentation in conjunction with the spacer of FIG. 1, according to another embodiment of the present disclosure.
Figure 18:
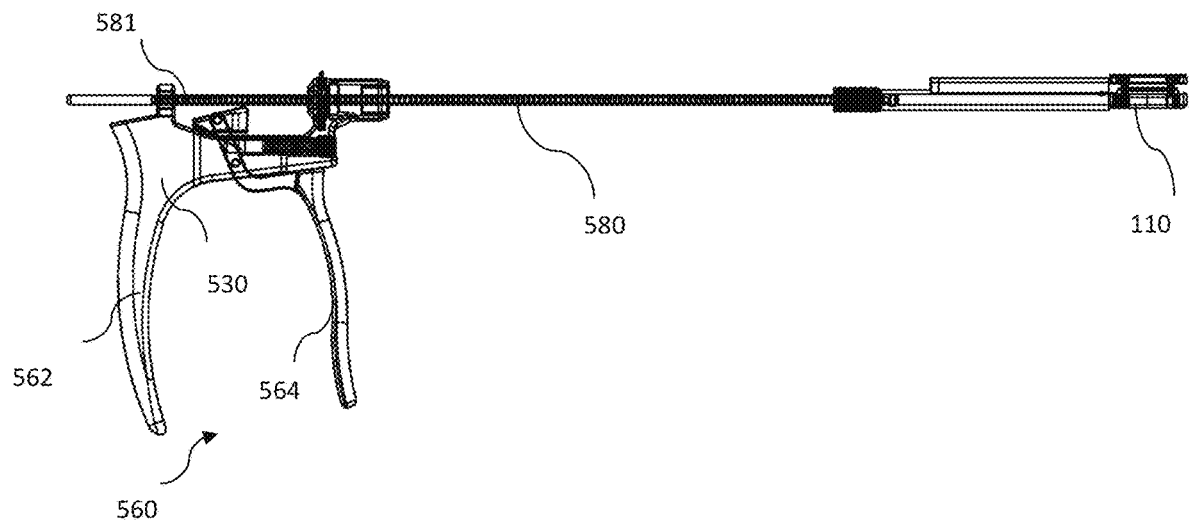
Figure 19:
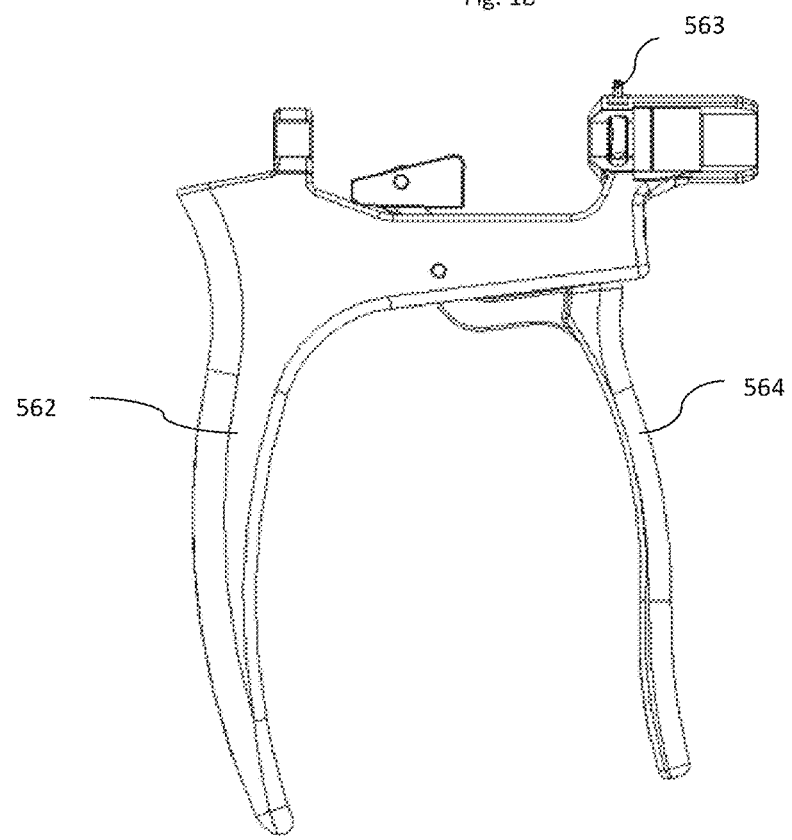

FIGS. 17-24 illustrate one embodiment of insertion system 500 for inserting any of the above described spacers into intervertebral space, as well as for injecting the hardening material into such implants. FIGS. 17-18 in fact show system 500 with spacer 110 attached thereto.

Generally, insertion system 500 of the present disclosure includes injector assembly 520 and insertion guide assembly 600. A similar injector assembly is described in U.S. Patent Publication No. 2015/0112352, filed on Oct. 22, 2014, and titled "Percutaneous Bone Graft Delivery System and Method," the disclosure of which is hereby incorporated by reference herein. As shown in FIGS. 17-18, injector assembly 520 includes handle subassembly 560 used to advance plunger shaft 580 distally.

Handle subassembly 560 includes fixed arm 562 and moving arm or trigger mechanism 564. Trigger mechanism 564 may be any type of trigger known in the art, for instance, the trigger mechanism may include a spring and/or a pivot pin on body 530 of the injector assembly that are actuated with the pulling of trigger mechanism 564. When trigger mechanism 564 is squeezed toward fixed arm 562, plunger shaft 580 extends distally. A ratchet subassembly allows for incremental movement of plunger shaft 580 and a release button 563, shown in FIG. 19, returns the injector assembly 520 back to its rest position when the button is deployed.

In one embodiment, the insertion system 500 may be bayoneted such that shaft 580 extends along an axis that is angled with respect to an axis along which fixed arm 562 extends. This configuration may allow for the length of shaft 580 to be offset from handle subassembly 560 and aid in visualization of a distal end of the shaft at a surgical site.

Figure 20:
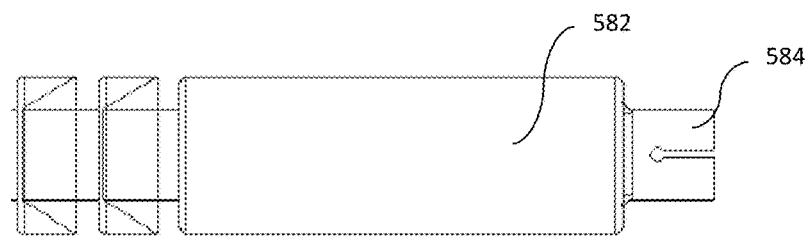
FIGS. 20-21 are side and top wire frame views, respectively, of the distal end of the injector assembly of the insertion instrumentation of FIG. 17.
Figure 21:
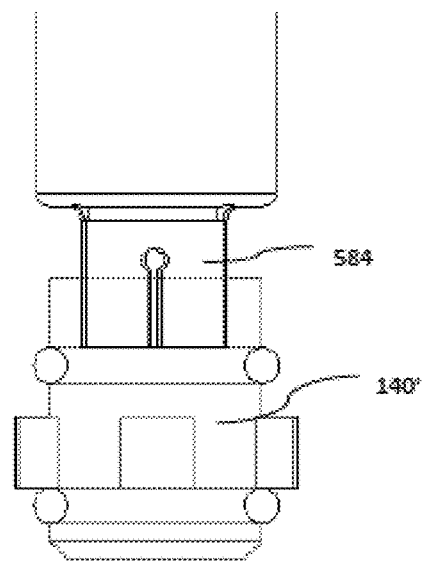

Plunger shaft 580 extends along a longitudinal axis from a proximal end 581 connectable to handle subassembly 564 to distal end 582. FIG. 20 shows distal end 582 of the plunger shaft 580, which includes split tip 584 for connection to the plug of the spacer, e.g. plug 140'. FIG. 21 shows the connection of the split tip 584 with plug 140'. In other embodiments, plunger shaft 580 may be threaded to cooperate with threads on the plug.

Figure 22:
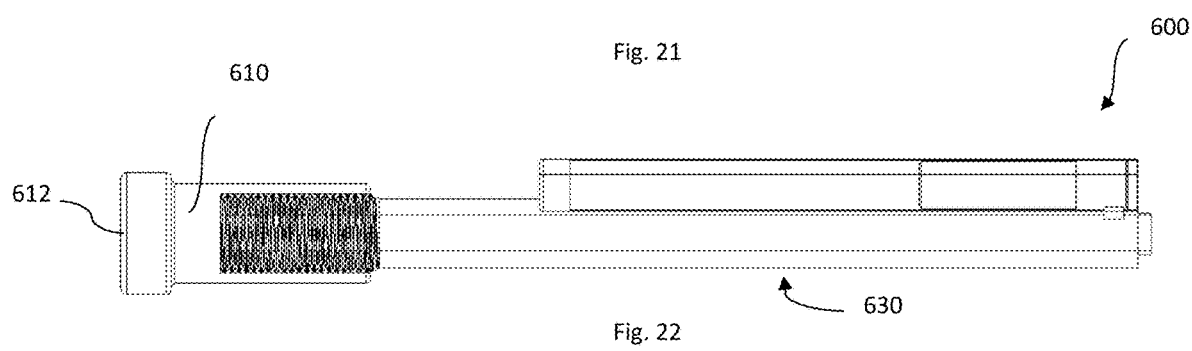
FIGS. 22-24 are side wire frame views of a guide assembly according to another embodiment of the present disclosure, FIG. 22 including an impaction handle and an inserter subassembly, FIG. 23 showing the inserter subassembly, and FIG. 24 showing the guide assembly with the spacer of FIG. 1 attached thereto.
Figure 24:
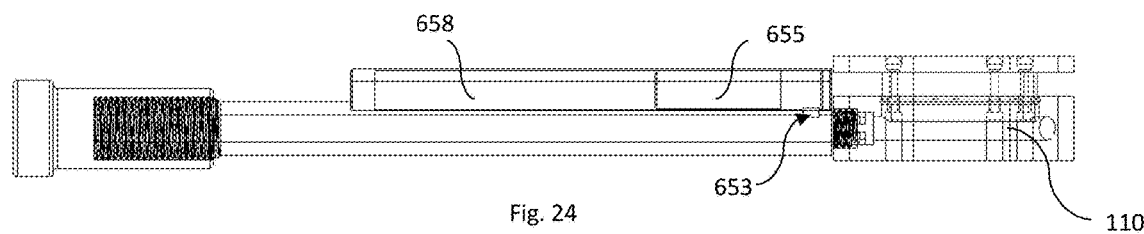

As shown in FIG. 22, guide assembly 600 includes impaction handle 610 at a proximal end of the guide 600 and an inserter subassembly 630 that may be in threaded engagement with the impaction handle. Impaction handle 610 allows for an impaction surface 612 for inline impaction to aid in the insertion of the implant. Inserter subassembly 630 provides for insertion of bone cement into the spacer at the surgical site and includes a collection tube 658, described in detail below, for collecting excess bone cement. Inserter subassembly 630 includes cannula 640 extending from a proximal end 641 to a distal end 643 and extends along a portion of the length of the inserter subassembly. At a distal end of inserter subassembly 630, cannula 640 leads into hollow connection member 645 for engagement with the injection port of the spacer, e.g. injection port 120 of spacer 110. Connection member 645 may be threaded for threaded engagement with the injection port of the spacer, e.g. injection port 120. FIG. 24 shows the guide assembly 600 with spacer 110 attached to the distal end and connection member 645.

Figure 23:
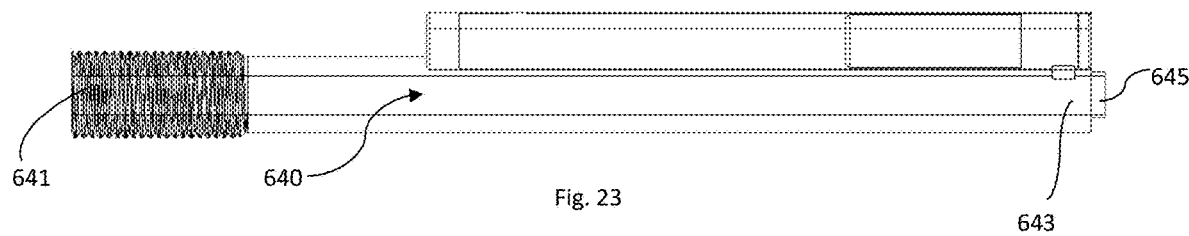

Hardening material, e.g. bone cement, is inserted in cannula 640 at proximal end 641 and flows through the cannula to the connection member 645 (best shown in FIG. 23). When the pressure in the spacer (e.g. spacers 110, 210, 310, 410) and cannula 640 exceeds a certain value, the material in the cannula flows through deflection hole 653 and into a one way pressure relief valve 655 to provide pressure relief. The valve 655 allows the material to flow in only one direction such that it does not enter the spacer. Under those circumstances, excess material can pass through the open valve so as to prevent over expansion of the implant. The material enters the valve and moves proximally, and the valve prohibits movement of the material back in the distal direction. The excess material passes through valve 655 and collects in collection tube 658.

Figure 25:
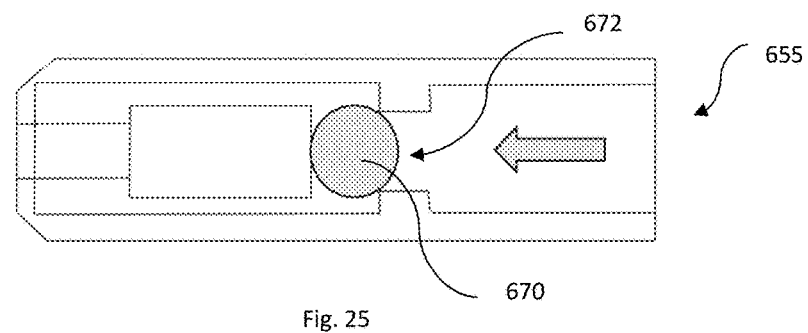
FIG. 25 is a side cross sectional view of a one way pressure relief valve of the inserter subassembly of FIGS. 22-24.

Any one way pressure relief valve known in the art may be used. In the illustrated embodiment, valve 655 includes a spring loaded ball 670, in sealing engagement with opening 672 of the valve. When the pressure is increased, the material (flowing from right to left in FIG. 25) pushes ball out of sealing engagement with opening 672, such that the material can move through the opening. When the flow of material ceases from right to left, in this example, the ball returns to its resting position in sealed engagement with opening 672 to prevent material to flow from left to right, to continue with this example.

In one embodiment, collection tube 658 may be detachable and attached to inserter subassembly by a sliding track assembly, as known in the art. The collection tube may further be disposable, such that it can be disposed after a single use after the excess material collects within it.

In another embodiment of the present disclosure, a method of implanting and expanding spacer 110 in TLIF surgery includes first removing at least a portion of an intervertebral disc between adjacent vertebrae using tools and techniques known in the art. Inserter subassembly 630 is attached to impaction handle 610 by a threaded engagement. Spacer 110 is then attached to the distal end of the inserter assembly 630 at connection member 645. Impaction surface 612 of the impaction handle 610 is then impacted, e.g. malleted, to insert the spacer 110 into the disc space. Impaction handle 610 is then unthreaded and disconnected from inserter subassembly 630. The proximal end 641 of cannula 640 is then filled with hardening material. The amount of hardening material can be determined by correlating cubic centimeters to millimeters of height expansion of the spacer. The inserter can be filled by any technique known in the art, and may depend on the surgeon's preference. For example, a syringe system can be used to deliver the material into the inserter. The syringe may be connected to the inserter directly. Plug 140 of the spacer 110 is then assembled to split tip 584 of the plunger shaft 580 and inserted into proximal end 641 of inserter subassembly and cannula 640.

Trigger mechanism 564 is then squeezed toward fixed arm 562 to advance the plunger shaft 580 distally. As the plunger shaft advances distally, plug 140 translates distally within cannula 640 and pushes the hardening material into the spacer 110. Once plug 140 cannot be advanced further, plunger shaft 580 is rotated 90 degrees clockwise and the plug is driven forward into the injection port 120. Plunger shaft 580 is rotated 90 degrees counter clockwise to lock the plug 140, 140' into the spacer 110. Although, different rotation directions and degrees can be used, so long as the plug is locked into the spacer. The angle and positioning of top component 124 can then be set before the material hardens and the spacer becomes rigid.

Figure 26:
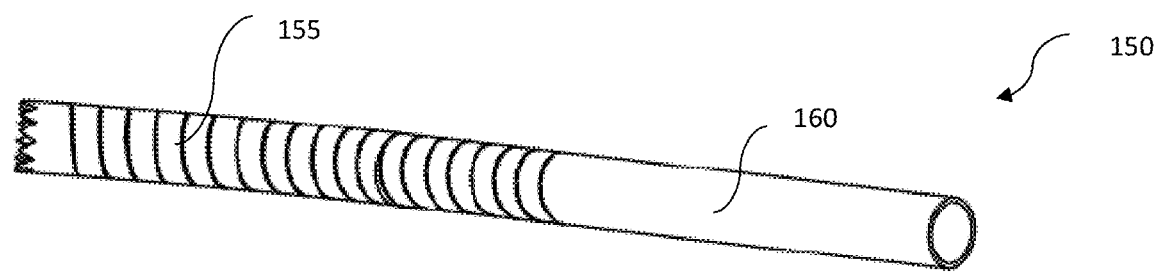
FIG. 26 is a coring tool to be used in conjunction with any of the spacers of the present disclosure according to another embodiment of the present disclosure.
Figure 27:
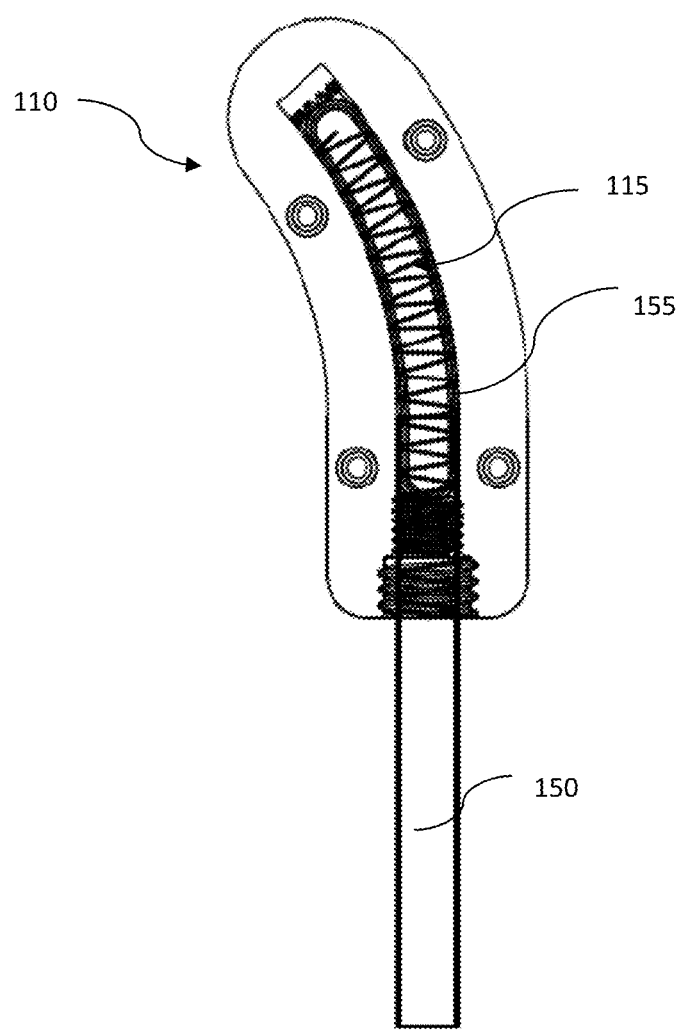
FIGS. 27-28 are top and side wireframe views, respectively, of the coring tool of FIG. 26 in conjunction with the spacer of FIG. 1.
Figure 28:
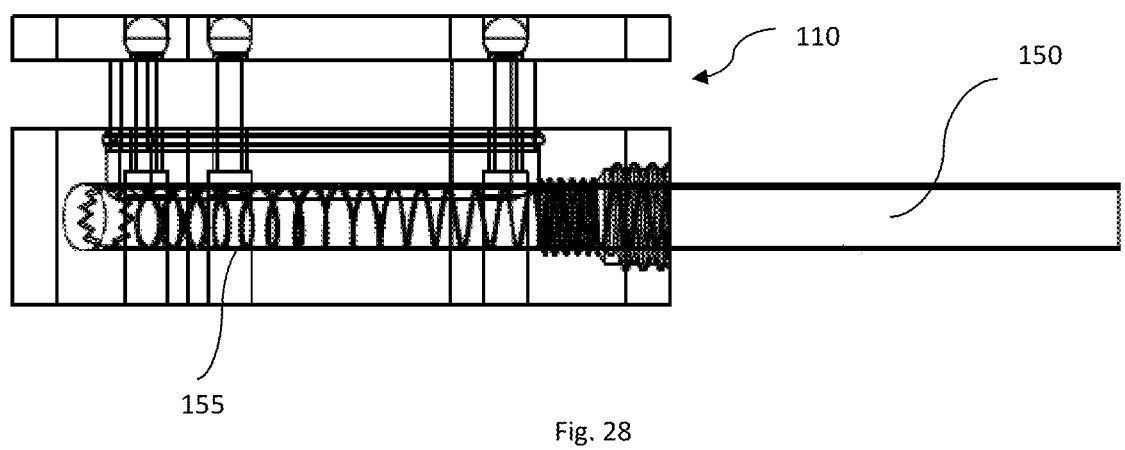

In another embodiment, FIGS. 26-28 show coring tool 150 to be used in conjunction with any of the above-described spacers. For instance, FIGS. 27-28 show the tool with spacer 110. Coring tool 150 is designed to be used after the hardening material has set and the spacer is rigid in order to aid in the collapse or contraction of the implant. For instance, coring tool 150 can be used during revision surgery to remove the hardening material from within spacer 110 or during a repositioning of the spacer 110 after the material has hardened. Coring tool 150 includes flexible portion 155 and solid portion 160. Flexible portion 155, as shown, is constructed by laser cutting metal tubing to a sufficient depth to allow flexing about the cut. The laser cut may extend circumferentially around the outer surface of the tubing and may have a wave or sinusoidal shape to enhance flexibility. In this manner, the laser cuts may define discrete segments that interlock with each other. In other examples, the laser cuts may be a single cut which moves along the tubing in a spiral pattern. The laser cuts may be at any depth relative to the thickness of the shaft, for example, cuts that score the outer surface, or cuts that extend deeper into the shaft. Flexible portion 155 may be integral with or otherwise attached (e.g., laser welded) to solid portion 160. Due to flexible portion 155, coring tool 150 can cut around bends, such as for example, curved channel 115 to remove the hardening material from the anterior-most area of the channel. Coring tool 150 may also be used in conjunction with an ultrasonic transducer to convert electrical energy into mechanical energy to break down the hardening material.

In another embodiment, a method of collapsing spacer 110 during a revision surgery or to reposition the spacer after the material has hardened includes removing plug 140, 140' from connection with the spacer. Because the plug is made from a material that does not adhere to the hardening cement, the plug can be removed by rotation of the plug, preferably about 90 degrees clockwise or counter-clockwise. The rotation can be in the opposite direction in which the plug was inserted. Channel 115 of the spacer 110 is then cored out using coring tool 150 and the hardened material is removed. With the spacer cored, top component 124 can be pushed downward and forced toward base component 112, such that the distance between the two components decreases. This is possible because the hardened material present in internal cavity 118 can be pushed into the now cored channel 115, thereby allowing the top component 124 to move downward with respect to base component 112. As such, spacer 110 collapses to a lower profile. The spacer can then be expanded to a different height, repositioned within the disc space, or removed.

It will be understood that the same or similar methods may be employed to also install, expand, and collapse spacers 210, 310, and 410. The methods can be employed at any level of the spine, and from any surgical approach without departing from the scope of the present disclosure. More specifically, it is contemplated that any of the spacers 110, 210, 310, 410 may be implanted from an anterior, posterior, posterior-lateral, lateral or other surgical approach.

The present disclosure may also include various systems and kits for implanting, expanding, and/or collapsing any of the above-described spacers. While it is envisioned that these various implants, materials, and instruments may be utilized, packaged, sold, or designed in any number of systems and kits, a few representative embodiments will be discussed below.

In one embodiment, the present disclosure can include a kit which can be packaged in a single package as a system or in multiple packages that can be selected as needed by the operator to form a system. For example, such a kit may include a plastic cannula, such as cannula 640, pre-filled with hardening material. The pre-packaged set can be offered in a sterile package. This allows the packaged kit, provided in a blister package for example, to be supplied to an operating room and opened immediately prior to use in a surgical procedure. In use, the cannula may have a break away tip that can be cut and the plastic cannula can be slid into the inserter subassembly 630 that is attached to the spacer. The plug of the spacer can be pushed down the cannula to move the material into the spacer. Once the spacer is expanded, the plug can be locked, and the cannula can be removed and disposed of.

In another embodiment, a kit of the present disclosure may include an expandable spacer and a flexible coring tool, as described above. In a further embodiment, the present disclosure includes a surgical implant system including at least one spacer, injector assembly, and insertion guide assembly. The system may further include a coring tool, as discussed above. The system may include hardening material. The system may include a surgical procedure that has instructions or protocol for using the implant, hardening material, and/or insertion and contraction instruments. The protocol may include aspects of any of the above-discussed embodiment, though other variations are also envisioned within the scope of the present disclosure.

Although the spacers discussed above are generally discussed as being capable of being placed within the space between adjacent vertebral bodies, it is contemplated to provide implants in accordance with the present invention that may expand up to the height of three or more vertebrae, enabling the spacer to function as a corpectomy cage. These implants may simply be larger in initial size or may include telescoping portions or the like to achieve the expansion necessary to span the space created by the removal of one or more vertebral bodies. It is to be understood that collapsing such an implant may require multiple coring processes like those described above. It could also be that larger coring tools or the like are to be utilized.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit for spinal surgery comprising:
an expandable spacer having a top component, and a base component in engagement with the top component, the base component defining at least one channel for receiving a hardening material, wherein placement of the hardening material within the channel causes the top component to move between a first position in which the top component is a first distance from the base component and a second position in which the top component is a second distance from the base component, the second distance being greater than the first distance; and
a coring tool adapted to remove the hardening material from the spacer after the hardening material has hardened.

2. The kit of claim 1, wherein the spacer includes an injection port in fluid communication with the at least one channel.

3. The kit of claim 2, wherein the spacer includes a locking plug engageable with the injection port.

4. The kit of claim 3, wherein when the locking plug is engaged with the injection port, the locking plug seals the hardening material in the spacer.

5. The kit of claim 3, wherein the locking plug is a threaded plug.

6. The kit of claim 3, wherein the locking plug has more than one projection so that rotating the plug ninety-degrees in a first direction locks the plug to the injection port and turning the plug ninety-degrees in a second direction opposite the first direction unlocks the plug.

7. The kit of claim 1, wherein when the hardening material hardens, the spacer is rigid.

8. The kit of claim 1, wherein the top component includes a top plate that is moveable with respect to the base component before the hardening material hardens.

9. The kit of claim 8, wherein the top component is connected to the base component by at least one securing member, the securing member configured to allow the top plate to move in different directions.

10. The kit of claim 9, wherein the securing member is a post including a rounded member connected to a first end of a shaft and a flange connected to a second end of the shaft.

11. The kit of claim 10, wherein a diameter of the shaft of the post is less than a diameter of the flange of the post.

12. The kit of claim 11, wherein the top component defines a first hole for engaging the rounded member of the post and the base component defines a second hole for engaging the flange of the post.

13. The kit of claim 12, wherein the second hole includes a step having a diameter less than the diameter of the flange, such that the step prevents the flange from translating out of the second hole.

14. The kit of claim 1, wherein the base component further comprises an internal cavity for receiving the top component, the internal cavity in fluid communication with the channel.

15. The kit of claim 14, wherein a diameter of the channel is greater than a diameter of the internal cavity.

16. The kit of claim 1, further comprising the hardening material.

17. The kit of claim 1, wherein the at least one channel is curved, and the coring tool includes a flexible portion adapted to fit in the curved channel.

18. A method for spinal repair comprising the steps of:
inserting a spacer at least partially into an intervertebral disc space; and
inserting hardening material into a channel of a base component of the spacer, the hardening material causing a top component of the spacer to move a distance from a first position to a second position, the top component being relatively further from the base component in the second position than in the first position; and
removing the hardening material with a chisel tool after the hardening material hardens.

19. The method of claim 18, further comprising the step of plugging the channel after the step of inserting the hardening material.

20. The method of claim 18, wherein the top component includes a top plate, and the method further comprises moving the top plate in a poster-anterior direction and/or lateral direction before the hardening material hardens.

* * * * *